United States Patent [19]

Ragot et al.

[11] Patent Number: 4,502,178
[45] Date of Patent: Mar. 5, 1985

[54] STAMPED CONNECTOR FITTINGS FOR WINDSCREEN WIPER ARMS

[75] Inventors: Roger A. Ragot, Orly; Claude J. Wolf, Chantilly, both of France

[73] Assignee: Equipements Automobiles Marchal, Issy-les-Moulineaux, France

[21] Appl. No.: 479,359

[22] Filed: Mar. 28, 1983

[30] Foreign Application Priority Data

Apr. 2, 1982 [FR] France ................. 82 05768

[51] Int. Cl.³ ............................................. B60S 1/40
[52] U.S. Cl. ................................. 15/250.34; 72/379
[58] Field of Search .......... 15/250.31, 250.32, 250.34, 15/250.35; 72/379, 336, 339

[56] References Cited

U.S. PATENT DOCUMENTS 2,215,371  9/1940  Horton ................ 15/250.34 X
3,769,654 11/1973  Edele et al. .......... 15/250.34
4,361,024 11/1982  Haldric .................... 72/379

FOREIGN PATENT DOCUMENTS 764101 12/1956  United Kingdom ............ 15/250.34

Primary Examiner—Peter Feldman
Attorney, Agent, or Firm—Brisebois & Kruger

[57] ABSTRACT

A connector fitting for mounting a windscreen wiper arm on the output spindle of a windscreen wiper arm drive mechanism is formed from sheet metal by stamping the outline of a blank, deforming the blank to form a fastening means for the blade-applying spring, chasing the metal to form a bush to receive the spindle and bearing collars for a pivot pin articulating the fitting to the blade, and folding the metal to give the fitting a channel shape.

15 Claims, 5 Drawing Figures

STAMPED CONNECTOR FITTINGS FOR WINDSCREEN WIPER ARMS

The present invention relates to a windscreen wiper arm comprising a stamped connector fitting for mounting the windscreen wiper arm on the output spindle of a driving mechanism. The invention also aims at a method for the production of a stamped fitting of this type.

It is known that the drive mechanism for motor vehicle windscreen wiper arms comprises, in general, a rotary spindle whereon there is assembled a connector fitting which is articulated on a mounting fixed to the windscreen wiper arm. A small cap allows the connector fitting to be concealed and is articulated in relation to the wiper arm mounting on the same pivot pin as the connector fitting itself. The prior art connector fittings are generally formed by a piece moulded from an alloy of the "Zamac" type. Such a fitting is constituted by (a) a zone, for fixing to the drive mechanism output spindle which has a serrated section to be engaged in a fructoconical bore in the said fixing zone of the fitting, whilst allowing a threaded part to project out of this zone to accommodate a fastening nut for locking the connector fitting on the output spindle and (b) an articulation zone of a prismatic external shape divided into two sides by a longitudinal slot. In these two sides are two coaxial bores within which there are disposed two bearing bushes to accommodate the pivot pin articulating the connector fitting to the windscreen wiper arm mounting. A semi-circular transverse slot centred on the axis of the pivot arm is arranged in the two sides so as to allow the edge of the cap to pass near the articulation portion of the connection fitting when the wiper arm mounting is subjected to rotation intended to enable the windscreen wiper blade to be removed from the windscreen. Between the sides of the connector fitting there is also loosely mounted a pulley of polytetrafluoroethylene on a transverse shaft which is intended to fasten a spring interposed between the connector fitting head and the wiper arm mounting. Such an embodiment of the connector fitting is expensive since, on the one hand, a moulding technique using a relatively expensive material is employed and, on the other hand, a considerable number of components must be attached to the moulded element.

The present invention aims to obviate these drawbacks by providing a connector fitting of moderate cost from a flat metal sheet by a relatively simple stamping technique.

Accordingly one aspect of the present invention provides a connector fitting for a windscreen wiper arm to connect the arm to the output shaft of a wiper drive mechanism, said connector fitting comprising: a fixing zone for the output shaft; an articulation zone for an articulation of the fitting relative to a cap and to a windscreen wiper arm mounting; and elastic means engaging both said connector fitting and said wiper arm mounting; wherein the connector fitting is formed from a stamped blank; wherein the fixing zone of said connector fitting has a substantially channel-shaped cross-section with a web having a substantially frustoconical collar; wherein the articulation zone of the connector fitting comprises in the extension of the flanges of the fixing zone two further flanges of an increasing height which are interconnected by a base disposed as an extension of the web of the fixing zone channel and in which two substantially coaxial openings are formed for the passage of a pivot pin intended to articulate the connector fitting to the windscreen wiper arm mounting; and wherein fastening means for said elastic means are arranged between said fixing zone and said articulation zone.

In a preferred embodiment, the pivot pin for articulating of the connector fitting to the wiper arm mounting also ensures articulation of a cap to the fitting, said cap being intended to cover the said connector fitting, the said flanges of the connector fitting extending in lugs shaped to define with the end edge of the articulation zone, a semi-circular slot concentric with the axis of articulation; the fastening means is formed by a loop projecting inwardly of the connector fitting; the free ends of the lugs are bent at right angles to form stops abutting on the inner side of the wiper arm mounting; each of the two substantially coaxial openings comprises a collar having an inner diameter which is slightly greater than that of the pivot pin; a notch is arranged externally on the connector fitting starting from the longitudinal edge of at least one side flange, this notch being intended to accommodate an internal catch engagement stud on one of the sides of the articulated concealment cap; the elastic means is constituted by a tension spring having one end hooked to the fastening means and its other end hooked on to the windscreen wiper arm which is fixed to the wiper arm mounting.

In a second embodiment, each of the two substantially coaxial openings comprises an externally extending collar forming a spacer at the articulation between the cap and the connector fitting.

In a third embodiment, there is inserted in each of the two substantially coaxial openings of the side flanges, a bush forming a bearing and having an inner diameter which is slightly greater than the diameter of the pivot pin.

In a variant which may be incorporated in any of the three above-mentioned embodiments, the lugs of the connector fitting may be interconnected at their free ends by a bar, preferably having a central notch in which the stem of the tension spring rests.

A second aspect of the invention provides a method for forming such a connector fitting for a windscreen wiper arm, having said lugs and semicircular slot, such method comprising stamping a blank from a disc of ductile metal or alloy; subjecting the blank to a punching operation so as to cut out said lugs of the connector fitting, the two substantially coaxial side openings of the flanges of the articulation zone and the corresponding opening of the substantially frustoconical collar of the fixing zone of the connector fitting; then shaping on the blank, by chasing of the metal, the collar of the fixing zone; imparting to said collar to the articulation zone an appropriate conicity; bending the blank on a jig so as to obtain the generally channel-shaped cross-section of the connector fitting; and finally effecting a punching operation between the fixing zone and the articulation zone so as to form the fastening means for the spring.

Where the side flanges of the articulation zone have external collars, the blank is inverted after the collar of the fixing zone has been formed, and the said external collars are formed by chasing of the metal before the bending on the jig.

It is also possible to form the internal collars after the blank has been bent on a jig in which case the jig comprises, a transverse hole of an appropriate diameter.

In a preferred mode of implementation of the method two blanks disposed together end to end are cut out flat; they are maintained connected together until the end of the forming operations and they are then separated by cutting out their connecting zone constituted by the ends of the lugs of the articulation zone of the two connector fittings formed in this way.

A third aspect of the invention provides a windscreen wiper arm for connecting the windscreen wiper backing strip to the output shaft of a windscreen wiper drive mechanism; said arm comprising a connector fitting to be fixed on the said output shaft, the said connector fitting being articulated in relation to the windscreen wiper arm mounting carrying the windscreen wiper backing strip; the connector fitting being in accordance with the first aspect specified above.

In order that the present invention may more readily be understood the following description is given, merely by way of non-restrictive example, with reference to the accompanying drawings in which.

Figure 1:
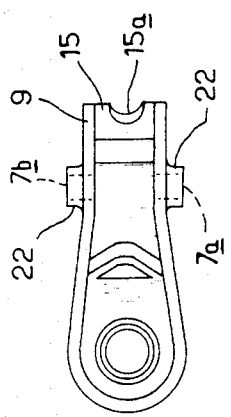
FIG. 1 is an underneath plan view of a connector fitting according to the invention, (i.e. viewed along the plane denoted by line I—I of FIG. 3)
Figure 2:
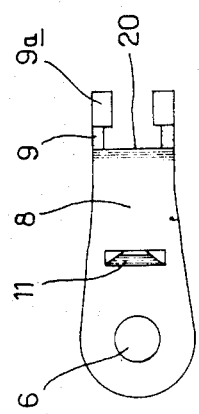
FIG. 2 is a top plan view of the connector fitting of FIG. 1, (i.e. viewed along the plane denoted by line II—II of FIG. 3)
Figure 3:
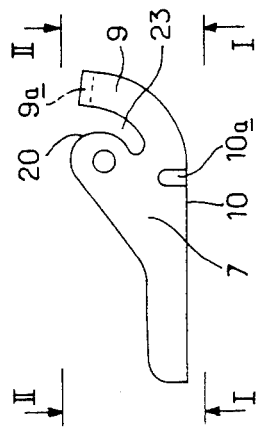
FIG. 3 is a side view of the connector fitting of FIG. 1, viewed along the plane denoted by line III—III of FIG. 2.

In the embodiment of FIGS. 1 to 3, the connector fitting according to the invention is generally designated 1. This connector fitting 1 comprises a fixing zone 2 for receiving the output spindle of the windscreen wiper drive mechanism (for example the driven shaft of the wiper motor) and an articulation zone 3 defining a common articulation for the windscreen wiper arm mounting 4 and the concealment cap 5.

The fixing zone 2 has, in cross-section, a substantially channel-shaped section whose web is provided on the inside with a frustoconical collar 6. The articulation zone 3 is situated in the extension of fixing zone 3 and comprises two parallel lateral flanges 7 interconnected by an upwardly sloping web 8. On each of the lateral flanges 7, there is arranged a circular opening 7a, 7b, edged by an inner bearing collar 21 which is coaxial with the corresponding bearing collar provided on the other flange. Each flange 7 ends in a lug 9 having at its end a tab 9a bent at right angles. Each supporting lug 9 defines with the edge 20 of the articulation zone 3, a semi-circular slot 23 concentric with the common axis of the bearing collars 21. On the longitudinal edge 10 of each flange 7 on the articulation zone 3 is a slot 10a to accommodate a catch engagement stud 5a provided on the inner wall of the concealment cap 5 when the cap is in position covering the connector fitting 1 and output spindle 13, 13a, 13b. Between the fixing zone 2 and articulation zone 3 is a V-shaped loop 11 whose tip is directed towards the inside of assembly head 1. This loop 11 is intended to fasten the end 16a of a tension spring 16 whose other end 16b is hooked in an opening 17a provided at the end of the windscreen wiper arm 17 which is fixed to the web of mounting 4 by rivetting at 17b.

The connector fitting 1 is obtained by the stamping of a disc of ductile metal. Two blanks of an appropriate shape are cut out head to tail by being submitted simultaneously to a stamping operation whilst arranging in a connecting zone between these two blanks (a) the outline of the lugs 9 of the connector fitting, (b) the outlines of the two side openings 7a, 7b, of the flanges 7 of the articulation zone and (c) the outline of the opening corresponding to the frustoconical collar 6 of the fixing zone 2 of the connector fitting. There are then formed by the chasing of the metal, the collar 6 of the fixing zone 2 and the inner bearing collars 21 on the flanges 7 at the articulation zone 3. The collar 6 of the fixing zone 2 is then given its appropriate conicity. Then the blank is bent on a jig so as to obtain the general channel shape of the connector fitting 1; finally, the punching operations between the fixing zone 2 and the articulation zone 3 are effected on the jig so as to form the fastening structure for the spring 16, that is to say, a V-shaped loop 11 whose tip is directed towards the inside of the connector fitting 1. The connecting zone of the two blanks which has been preserved until the completion of the forming operations is then severed; this zone constitutes the ends of the lugs 9 of the articulation zone 3 of the two connector fittings 1 formed in this way.

It if is intended to have external collars 22 on the flanges 7 of the articulation zone, the blank is merely inverted, after the collar 6 of the fixing zone has been formed, and the said collars can then be formed by chasing the metal; the production process can then be continued by the bending operation on the jig, as set out above.

The inner collars 21 may also be formed after the blank has been bent on the jig, in which case the jig will comprise a transverse hole of the appropriate diameter. This procedure avoids the need for realigning the axes of the two collars of the flanges after bending.

The connector fitting 1 is assembled with its cap 5 and wiper arm mounting 4 by means of an articulation pin 12 which is positioned in the two bearing collars 21 and which is locked in position by crimping. The two ends of the tension spring 16 are then fastened on the loop 11 and in the opening 17a of arm 17, respectively. To install this windscreen wiper blade on a vehicle, the connector fitting 1 is force-fitted, via collar 6 of its fixing zone 2, on the serrated part 13a of the output spindle 13 of the windscreen wiper drive mechanism so as to allow the threaded end portion 13b of the spindle 13 to project outwardly through the collar 6 to receive the fixing nut 14. It will be seen that during the fixing of connector fitting 1 on spindle 13 it was possible to retract the cap 5 by rotation around the articulation pin 12 because its edge which is nearest to this articulation pin was capable of sliding into the semi-circular slot 23 bounded by the lugs 9 and edge 20 of the articulation zone 3 carrying the said lugs. This movement of the cap 5 is also effected when the wiper arm mounting 4 is rotated around pivot pin 12 to move the windscreen wiper blade clear of the windscreen glass, for example for cleaning the windscreen.

Figure 5:
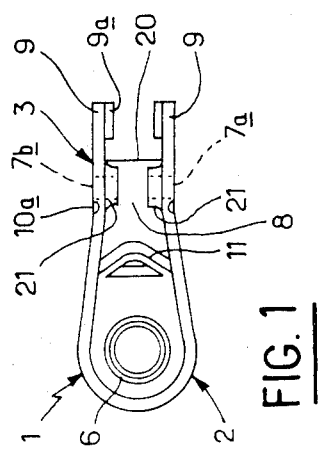
FIG. 5 is a top plan view of a variant of the embodiment of the connector fitting of FIGS. 1 to 3.
Figure 4:
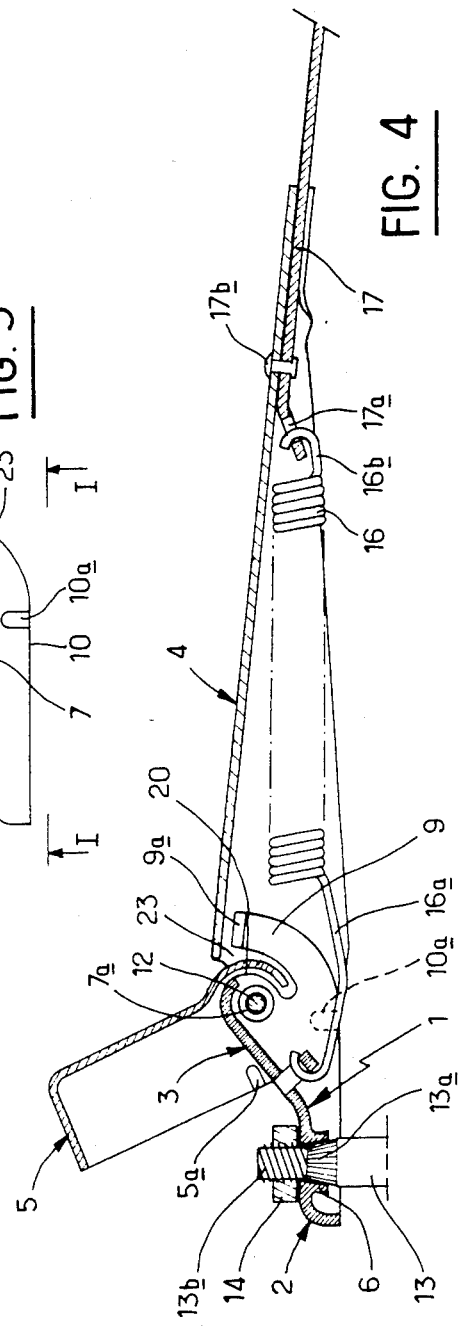
FIG. 4 is a longitudinal sectional view, with the spindle concealment cap raised, of a windscreen wiper arm incorporating the connector fitting of FIGS. 1 to 3.

In the variant shown in FIG. 5, the bearing collars on the flanges 7 around the openings 7a, 7b of the articulation zone 3 are external collars 22 which constitute distance pieces between the cap 5 and fitting 1. In this variant a spacer 15 is provided between the lugs 9, this spacer being obtained by a cutting step during the manufacture of the flat blank. This spacer 15 is provided on its lower side with a small notch 15a intended to centre the end 16a of the tension spring 16, this end 16a being fastened on the V of the loop 11. Spacer 15 increases the bearing surface of fitting 1 within the arm mounting 4 and obviates the need for reinforcing the arm mounting in the bearing zone of lugs 9 which would frequently be necessary if the lugs 9 are not provided with spacers (because of the considerable force of tension spring 16).

It shall be duly understood that the embodiments described above are in no way restrictive and may give rise to any desirable modifications without departing thereby from the scope of the invention as defined by the following claims. For example the loop 11 may no longer form a V-shaped projection as described above, but may comprise either an opening in the web of the channel constituting the fitting 1, or may be in the form of a hollow stamped zone which projects from that side of fitting 1 where the spring 16 is fastened and which has an opening for the penetration of the hooked end 16a of the spring.

We claim:

1. A stamped metal connector fitting for a windscreen wiper arm for mounting the arm on an output spindle of a windscreen wiper drive mechanism, said connector fitting being stamped from a metal sheet and including a fixing zone for securing the connector to the output spindle, and an articulation zone for pivotally connecting a wiper arm casing to the fitting itself, said connector fitting comprising, a U-shaped body having side walls and a top wall, and said side walls in the fixing zone extending only partly around the spindle and being open in a direction toward the articulation zone, said top wall in the fixing zone have formed therein an integral collar of a height greater than the thickness of said top wall and having an opening therein of truncated section for mounting on a serrated portion of the output spindle, said side walls, in said articulation zone having a thickness essentially the same as the side walls in the fixing zone and increasing in height from the fixing zone to the articulation zone, said side walls having aligned openings therein, in the articulation zone, for receiving a pivot pin for pivotally connecting the wiper arm casing to the connector, and means between the collar and the openings for receiving the pivot pin for pivoting the wiper arm casing, for connecting an end of a spring to the connector for forcing the wiper arm toward a windshield.

2. A connector fitting according to claim 1 wherein said means for connecting an end of the spring comprises an integral struck out portion defining an opening for receiving an end of the spring.

3. A connector fitting according to claim 1 wherein the pivot pin for pivotally connecting the connector fitting to the wiper arm casing also pivotally connects a cap to the fitting for covering said fitting; lug means formed in at least one of said side walls, and an arcuate slot between said lug means and said openings for said pivot pin and concentric with the openings for the pivot pin, said slot comprising means to receive a wall of the cap to permit pivoting the cap to an uncovered position on said fitting.

4. A connector fitting according to claim 1 wherein said means for connecting the spring comprises a loop deformed from said connector fitting and projecting inwardly of the side walls thereof.

5. A connector fitting according to claim 3 wherein said lug means have ends bent at right angles so as to form stop means to abut an inner surface of the wiper arm casing to limit the extent of pivotal movement of the casing relative to the connector fitting.

6. A connector fitting according to claim 1 further comprising an integral collar bordering each of the openings for receiving the pivot pin, each collar having an inner diameter which is slightly greater than the diameter of the pivot pin.

7. A connector fitting according to claim 1 wherein the pivot pin for pivotally connecting the connector fitting to the wiper arm casing also pivotally connects a cap to the fitting for covering the fitting, at least one recess in a side wall of the connector fitting, and an indentation in said cap engagable in the recess to retain the cap in a covering position on the connector fitting.

8. A connector fitting according to claim 2 wherein a first end of a spring is hooked on the struck out portion, and a second end of the spring is hooked to the windscreen wiper arm at a location spaced from the connector fitting.

9. A connector fitting according to claim 6 wherein each collar extends outwardly of the connector fitting.

10. A connector fitting according to claim 5 wherein said lug means of the connector fitting comprise ends integrally connected by a bar.

11. A connector fitting according to claim 10 wherein said bar has midway therealong a notch to center an end of a spring connected to the connecting means.

12. A method for forming a connector fitting for a windscreen wiper arm according to claim 1, comprising the steps of:
(a) stamping a blank from metal;
(b) punching said blank to form therein the openings for receiving the pivot pin and the opening for mounting the connector fitting on the spindle;
(c) further shaping the blank to form a collar around the opening for mounting the connector fitting on the output spindle;
(d) forming said opening of truncated section in said collar;
(e) bending the blank to form the U-shaped body;
(f) punching the blank to form the connecting means for connecting an end of a spring to the connector fitting.

13. A method according to claim 12 wherein said step (f) comprises punching a V-shaped loop directed inwardly of the connector fitting.

14. A method according to claim 12 further comprising forming external collars around the pin receiving openings.

15. A method according to claim 12 further comprising forming internal collars around the pin receiving openings.

* * * * *